United States Patent
Bragger et al.

(10) Patent No.: US 12,005,100 B2
(45) Date of Patent: Jun. 11, 2024

(54) COMBINATION, THERAPEUTIC USES AND PROPHYLACTIC USES

(71) Applicant: Quantec Limited, Hamilton (NZ)

(72) Inventors: Judith Mary Bragger, Hamilton (NZ); Rodney Wayne Claycomb, Hamilton (NZ); Colin Roger Ogle, New Zealand (NZ)

(73) Assignee: Quantec Limited, Hamilton (NZ)

( * ) Notice: Subject to any disclaimer, the term of this patent is extended or adjusted under 35 U.S.C. 154(b) by 20 days.

(21) Appl. No.: 16/094,058

(22) PCT Filed: Apr. 21, 2017

(86) PCT No.: PCT/NZ2017/050043
§ 371 (c)(1),
(2) Date: Oct. 16, 2018

(87) PCT Pub. No.: WO2017/183996
PCT Pub. Date: Oct. 26, 2017

(65) Prior Publication Data
US 2019/0134168 A1    May 9, 2019

(30) Foreign Application Priority Data
Apr. 21, 2016 (NZ) .................................. 719276

(51) Int. Cl.
| A61K 38/54 | (2006.01) |
| A61K 35/20 | (2006.01) |
| A61K 38/18 | (2006.01) |
| A61K 38/44 | (2006.01) |
| A61K 39/00 | (2006.01) |
| A61K 45/06 | (2006.01) |
| A61P 31/04 | (2006.01) |
| C07K 16/04 | (2006.01) |

(52) U.S. Cl.
CPC .............. *A61K 38/54* (2013.01); *A61K 35/20* (2013.01); *A61K 38/18* (2013.01); *A61K 38/1808* (2013.01); *A61K 38/44* (2013.01); *A61K 45/06* (2013.01); *A61P 31/04* (2018.01); *C07K 16/04* (2013.01); *A61K 2039/505* (2013.01)

(58) Field of Classification Search
None
See application file for complete search history.

(56) References Cited

U.S. PATENT DOCUMENTS

| 4,726,948 A | 2/1988 | Prieels et al. | |
| 2012/0244226 A1* | 9/2012 | Claycomb ............... | A61P 29/00 424/535 |

FOREIGN PATENT DOCUMENTS

| CN | 101494970 A1 | 7/2009 |
| EP | 2127667 A1 | 2/2009 |
| WO | 1996013271 A1 | 5/1996 |
| WO | 2007142542 A2 | 12/2007 |
| WO | 2010134827 A1 | 11/2010 |

OTHER PUBLICATIONS

Cleveland Clinic (https://my.clevelandclinic.org/health/diseases/22961-candida-albicans accessed Oct. 7, 2022).*
Bo Lonnerdal, "Nutritional and Psychological Significance of Human Milk Proteins", American Journal of Clinical Nutrition, 2003, vol. 77(suppl), 1537S-43S, USA.
Tripathi V. et al., "Bioactive Compounds of Colostrum and It's Application", Food Review International, 2006, vol. 22 pp. 225-244.
D'Amato, D. et al. "Enzymes and Enzymatic Systems as Natural Antimicrobials", Application of Alternative Food-Preservation Technologies to Enhance Food Safety & Stability, 2010 pp. 58-82.
D. A. Clare et al., "Biodefense Properties of Milk The Role of Antimicrobial Proteins and Peptides", Current Pharmaceutical Design, 2003, 9, 1239-1255.
M. Killan et el., "The oral microbiome—an update for oral healthcare professionals", British Dental Journal, vol. 221, Nov. 2016, pp. 657-666.
Zhi Y. Kho et al., "The Human Gut Microbiome—A Potential Controller of Wellness and Disease", Frontiers in Microbiology, Aug. 2018, pp. 1-23.
Brigitte Dreno et al., "The Skin Microbiome: A New Actor in Inflammatory Acne", American Journal of Clinical Dermatology, Sep. 2020.
Gregor Reid et al. "Microbiota restoration: natural and supplemented recovery of human microbial communities", Nature Reviews, Microbiology, Nov. 2010, pp. 27-38.
H. Kong et al., "Temporal shifts in the skin microbiome associated with disease flares and treatment in children with atopic dermatitis", Genome Research, 2012, pp. 850-859.
Wei et al., "Influence of milk-derived lactoferrin on intestinal microbial flora in mice," *Science and Technology of Food Industry*, vol. 34, No. 13 (2013) 5 pp.
Liu, "Study on Rapid Diagnosis and Chinese Medicine Treatment of *Candida albicans* Mastitis in Dairy Cows," Chinese Master's Theses Full-text Database, 2009, No. 2, pp. 10-12.

* cited by examiner

*Primary Examiner* — Julie Ha
*Assistant Examiner* — Tara L Martinez
(74) *Attorney, Agent, or Firm* — Leydig, Voit & Mayer, Ltd.

(57) ABSTRACT

This invention relates to the therapeutic and prophylactic use of a combination including lactoperoxidase and at least one other component, with an isoelectric point of, or substantially above 6.8, and which are extracted from milk, to modulate the microbiome of an animal by selectively against at least one pathogenic microorganism.

13 Claims, 6 Drawing Sheets

COMBINATION, THERAPEUTIC USES AND PROPHYLACTIC USES

CROSS-REFERENCE TO RELATED APPLICATIONS

This United States application is the National Phase of PCT Application No. PCT/NZ2017/050043 filed 21 Apr. 2017, which claims priority to New Zealand Patent Application No. 719276 filed 21 Apr. 2016, each of which is incorporated herein by reference.

BACKGROUND OF THE INVENTION

Technical Field

This invention relates to a combination, such as a composition, and its therapeutic and prophylactic uses. In particular (although not exclusively) the invention relates to a new method to modulate or treat the microbiome of an animal through selectivity towards micro-organisms.

Background Art

Humans and other animals host a very large variety of micro-organisms, both commensals and pathogenic. Commensal micro-organisms are those which live harmoniously with the host organism, utilising food or other benefits, without hurting it and often beneficially helping it. Oppositely, pathogenic micro-organisms, including bacteria, fungi, or a virus, are organisms which, after invading the body, typically lead to infection and associated conditions or diseases. Occasionally, commensal micro-organisms that are beneficial can take the opportunity to become pathogenic, in which case the commensals can be referred to as 'opportunistic commensals.'

Collectively, the term microbiota describes the community of both commensals and pathogenic micro-organisms that live on or in our bodies. The term microbiome is related to microbiota, but is often considered to describe the collective genomes of the micro-organisms, rather than the micro-organisms themselves. Throughout this specification, we will use the term microbiome, but this should be understood to encompass both the genetic and/or phenotypic diversity of the micro-organisms.

The microbiome can be very diverse, and is present on a number of areas of the body including the skin, different areas of the gastrointestinal tract from the oral cavity or mouth through to the rectum, nasal cavities, ears, lungs and vagina. The different environments at each location leads to competition and adaptation of the micro-organisms for survival. Additionally, in a healthy host, innate mechanisms help to selectively favour survival of commensals or health-giving microbes opposed to pathogenic microbes.

Research has established that a healthy microbiome is very important for metabolism of carbohydrates and proteins, development of the immune system, functioning of the epithelium, hormone production, vitamin production, pathogen protection and fat storage. (Hooper et al, 2004, Stappenbeck et al, 2004).

In the gut, the mucosal surfaces of the mouth, alimentary tract and colon are covered by a heavy load of endogenous bacteria that provide protection and a barrier against pathogenic organisms and food antigens. An immune tolerance to endogenous bacteria and food antigens exists so that the systemic adaptive immune system does not overreact to these antigens while maintaining reactivity to pathogenic bacteria. Any disruption of the barrier, caused for example by an acute episode of infectious gastroenteritis, bacterial overgrowth or a dose of antibiotics, leads to inflammation and the influx of cytokines. Inflammation interrupts the immune tolerance and may result in irritable bowel disease (IBD), a chronic inflammatory disorder of the intestines, characterised by pain, rectal bleeding, severe diarrhoea and weight loss.

In the mouth, periodontal disease has been considered to be an infection with specific causative bacteria, however many periodontic bacteria are now considered to be permanent commensal bacteria rather than transient pathogens. The microbiota of the human oral mucosa consists of a myriad of bacterial species that normally exist in commensal harmony with the host. For example, *Porphyromonas gingivalis* can be isolated from healthy individuals, but is involved in severe periodontal disease in some individuals with inflammation and loss of bone.

The skin is also colonised by a dense community of commensal organisms that occupy the skin and directly protect against pathogenic invaders by inhibiting colonization with pathogens through nutrient competition (Bibel et al., 1983) and through the production of antimicrobial peptides (AMPs) that inhibit pathogenic organisms (Cogen et al., 2010). *Staphylococcus epidermidis* produce high amounts of AMPs to control the growth of pathogenic *S. aureus* strains.

The bacteria that we usually identify with skin infections are a small fraction of the total population. Coagulase negative Staphylococci, such as *Staphylococcus epidermidis* and *Staphylococcus hominis*, are a substantial proportion of the commensals that predominate in the dry areas of skin. Lipophilic organisms such as *Propionibacterium* spp and *Malassezia* spp. predominate in sebaceous areas and moist, non-sebaceous areas are more likely to be inhabited by yeasts such as *Candida* or fungi such as *Trichophyton* spp. While these are ubiquitous and generally benign, commensal bacteria are often implicated in skin diseases when the skin barrier is compromised or broken. Optimal skin health is maintained when the microbiome and the immune system of the skin are balanced. Commensal microbes bridge the innate and the adaptive immune system and protect against atopic sensitisation and inflammation.

The removal of commensal organisms, such as *S. epidermidis*, through overuse of topical antibiotics may be detrimental to the host for two reasons. Firstly, removing *S. epidermidis* eliminates the bacterium's endogenous antimicrobial peptides, allowing potentially pathogenic organisms to colonize the skin more effectively. Secondly, without bacterial priming of the skin, the host may be less efficient in warding off infection.

With knowledge of the importance of the microbiome, researchers have been investigating how to modulate it in order to maintain or improve overall health, defend or treat against infection and associated diseases or conditions.

The most commonly relied on approach are use of antibiotics, which has been instrumental to modern medicine, both in terms of fighting infections that may otherwise kill a host, as well as allowing surgeries to be performed without major risk of subsequent infection and death. However, a major downfall of antibiotics, of course besides development of resistance, is that the antibiotics have little to no selectivity—such that the drug essentially kills all the microbiome, including the beneficial commensals. This is undesirable given the important functions of the microbiome as discussed previously.

Other approaches include the use of prebiotics and probiotics, which are thought to help modulate the microbiome. Prebiotics aim to provide optimal growing conditions for commensals. Probiotics include actual micro-organisms with the aim of populating the body's microbiome with specific species with apparent beneficial outcomes. Synbiotics include a combination of pre- and probiotics. Although these approaches hold promise, there is little scientific evidence yet of the therapeutic effectiveness of modulating microbiomes for key desired health outcomes. Furthermore, although pre- and probiotics may help boost the system's defense system, it has little to no potency for treating an infection that has already manifested.

WO 2014/159659 describes a composition using a chelator and a base to selectively target pathogenic bacteria in dental diseases. A number of potential compounds are listed as potential enhancers, without any specific anti-microbial effect, but which enhances the effect of the chelator or base in some way. Yet, most of the enhancers were not investigated or shown to improve therapeutic effectiveness. Furthermore, there is no suggestion that the compositions used in WO 2014/159659 have selectivity to the microbiome outside the dental environment.

WO 2011022542 has attempted to develop compositions with improved selectivity by relying on host-derived factors specific to each microbiome location, for instance in the mouth, skin, and airways. For instance, it discloses the use of salivary digestive products like maltose, maltotriose and dextrin to selectively modulate and promote commensals in the mouth. It also broadly suggests a range of other compounds with which may have additional benefits. There are seven example compositions provided, but without any analysis of whether these effectively work or impart any selectively towards commensals vs pathogenic micro-organisms. Furthermore, WO 2011022542 teaches towards development of specific compositions with different active agents for each location of treatment. This can be seen as a complicated and undesirable system which requires very different components to be used as active ingredients for different locations.

A different line of scientific study has investigated the proteins and peptides of the innate defense system which are present throughout the body in all mammals. It is the first defense against the invasion of pathogens, is present in all parts of the body at all times and is independent of a systemic adaptive immune system. It is non-inflammatory because it does not invoke the production of cytokines and anti-inflammatory because it takes up free radicals.

The innate defense system is particularly important in the eyes, mouth and respiratory tract where there is high risk of the entry of harmful pathogens. These areas are protected by a constant flow of liquid (tears, saliva and mucous) containing a high concentration of the proteins, peptides and defensins of the innate system, and substrates such as thiocyanate, that are required by the peroxidase enzyme to produce hypothiocyanite.

Under this category, EP 0614352 describes a dentrifice composition that includes an oxidoreductase enzyme and its substrate in order to develop hydrogen peroxide once administered, thereby providing an antimicrobial effect from hypothiocyanite ion production. A number of oxidoreductase options are provided, including glucose oxidase as the preferred enzyme, together with its preferred substrate, glucose. As illustrated by Example E, other ingredients such as peroxidase may also be added in attempt to convert thiocyanate ions, in the presence of hydrogen peroxide, into hypothiocyanite ions. Although the compositions are shown to produce hydrogen peroxide, there is no evidence to show whether any compositions imparted any degree of selectivity towards pathogenic micro-organisms instead of commensals. There is also no data to support whether addition of a peroxidase improves or imparts any selectivity. Furthermore, there are a wide number of synthetic excipients used, and there would appear a need to isolate or source each individual component before formulating the compositions.

As another example, U.S. Ser. No. 08/480,357 describes an approach to selectively target pathogenic micro-organisms with an apparent lack of inhibition towards commensals. The document highlights that myeloperoxidase, in the presence of a peroxide generator (e.g. glucose oxidase) and halide such as $Cl^-$ or $Br^-$; provides some selectivity towards certain pathogens whilst apparently avoiding inhibition of specific commensals. However, there are wide variations between myeloperoxidase and other peroxidases tested in terms of selectivity and potency between pathogens, the binding data is often contradictory to the inhibitory results or suggestive of poor selectivity towards specific pathogens. Lactoperoxidase showed very poor binding selectivity in comparison (as shown in Table 13), suggestive of it having little to no inhibition or selectivity, albeit not actually tested by the authors. At best, U.S. Ser. No. 08/480,357 may motivate a reader to explore myeloperoxidase (or perhaps eosinophil peroxide as per the claimed invention in claim 1) usage together with a peroxide and halide to achieve the reported results. Regardless, this document does not report ideal selectivity results across a broad range of pathogenic bacteria together with a lack of inhibitory effects towards a broad range of commensals.

In the case of the mammary gland, all of the components of its innate defense system have been extensively studied, especially the major components from milk such as lactoferrin, lactoperoxidase and angiogenin (Ribonuclease). There are many publications describing activity of these proteins against bacteria, yeast, fungi and viruses. However none of these publications teach towards selectivity between commensals and pathogens, or the use of these components to modulate a microbiome.

In summary, new methods need to be developed to effectively modulate the microbiome without the harshness and lack of selectivity of antibiotics, and equally with greater potency than pre- and pro-biotics to selectively inhibit pathogenic micro-organisms without a similar level of inhibition of the beneficial commensals. Furthermore, there is a need to address the shortcomings as discussed above in relation to WO 2011022542, WO 2014/159659, EP 0614352 and U.S. Ser. No. 08/480,357. Ideally, the approaches should rely on natural based compositions for consumer acceptance and avoidance of side effects. Preferably, the components are easy to source, extract and are shelf-stable. If possible, the compositions should have wide coverage of selectivity so that a similar composition may be used to modulate the microbiome in a number of different locations on or in the body.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided a use of a combination, such as a composition, which includes lactoperoxidase and at least one other component, wherein the lactoperoxidase and at least one other component have an isoelectric point of or above substantially 6.8 and which are extracted from milk,
wherein the combination, such as a composition, is applied externally or internally to an animal to selectively inhibit growth or kill at least one pathogenic micro-organism without a comparative inhibition of at least one commensal micro-organism.

In one aspect the invention provides the use of a combination including lactoperoxidase and at least one other component, wherein the lactoperoxidase and at least one other component have an isoelectric point of or above substantially 6.8 and which are extracted from milk, to selectively inhibit growth or kill at least one pathogenic micro-organism without a comparative inhibition of at least one commensal micro-organism, by administering the lactoperoxidase and at least one other component to an animal.

According to a further aspect of the present invention there is provided a use of a combination, such as a composition, which includes lactoperoxidase, together with at least one or more of lactoferrin, angiogenin, and/or lysozyme-like protein, all having an isoelectric point of or above substantially 6.8 and which are extracted from milk, wherein the combination, such as a composition, is applied externally or internally to an animal to selectively inhibit growth or kill at least one pathogenic micro-organism without a comparative inhibition of at least one commensal micro-organism.

According to a further aspect of the present invention there is provided a use of a combination, such as a composition, which includes lactoperoxidase, lactoferrin, angiogenin, and lysozyme-like protein, all having an isoelectric point of or above substantially 6.8 and which are extracted from milk, wherein the combination, such as a composition, is applied externally or internally to an animal to selectively inhibit growth or kill at least one pathogenic micro-organism without a comparative inhibition of at least one commensal micro-organism.

According to a further aspect of the present invention there is provided a use of a combination, such as a composition, which includes lactoperoxidase, lactoferrin, angiogenin, and lysozyme-like protein, quiescin, and jacalin-like protein, all having an isoelectric point of or above substantially 6.8 and which are extracted from milk,
wherein the combination, such as a composition, is applied externally or internally to an animal to selectively inhibit growth or kill at least one pathogenic micro-organism without a comparative inhibition of at least one commensal micro-organism.

According to a further aspect of the present invention there is provided a use of a combination, such as a composition, which includes substantially all proteins isolated from milk which have an isoelectric point of or above substantially 6.8,
wherein the combination, such as a composition, is applied externally or internally to an animal to selectively inhibit growth or kill at least one pathogenic micro-organism without a comparative inhibition of at least one commensal micro-organism.

According to a further aspect of the present invention there is provided a use of a combination, such as a composition, substantially as herein described,
wherein the combination, such as a composition, is applied externally or internally to an animal to selectively inhibit growth or kill at least one pathogenic micro-organism without a comparative inhibition of at least one commensal micro-organism.

According to a further aspect of the present invention there is provided a method of modulating a microbiome by selectively inhibiting growth or killing at least one pathogenic micro-organism without a comparative inhibition of at least one commensal micro-organism characterised by the step of:
a) administering a combination, such as a composition, substantially as herein externally or internally to an animal.

In one aspect the invention provides a method of modulating a microbiome by selectively inhibiting growth or killing at least one pathogenic micro-organism without a comparative inhibition of at least one commensal micro-organism, the method including the step of administering to an animal a combination including lactoperoxidase and at least one other component, wherein the lactoperoxidase and at least one other component have an isoelectric point of or above substantially 6.8 and which are extracted from milk.

According to a further aspect of the present invention there is provided a method of treating or preventing a condition or disease in an animal that has at least a partial causative association with a microbiome in at least one location on or in the animal, characterised by the step of:
a) administering a combination, such as a composition, as described herein applied externally or internally to an animal.

In one aspect the invention provides a method of treating or preventing a condition or disease in an animal that has at least a partial causative association with a microbiome in at least one location on or in the animal, the method including the step of administering a combination including lactoperoxidase and at least one other component, wherein the lactoperoxidase and at least one other component have an isoelectric point of or above substantially 6.8 and which are extracted from milk.

In one aspect the invention provides a method of treating or preventing a condition or disease in an animal that has at least a partial causative association with a microbiome in at least one location on or in the animal, the method including the step of administering a combination substantially as described herein.

In summary, the inventors have discovered that the combinations, such as the compositions, as described herein have a spectacular and unexpected selectivity towards inhibition of pathogenic micro-organisms compared to a considerably less inhibitory effect towards beneficial commensal micro-organisms that are present in a health microbiome. The discovery presents itself towards new uses for modulating microbiomes, and/or preventing or treating associated conditions or diseases. Furthermore, the invention provides a significant advantage over previous methods of treatment such as broad spectrum antibiotics which do not have a high degree of specificity. The invention is also hugely beneficial in the sense that the combination, such as the composition, may be developed easily using known techniques and includes proteins derived from milk that have a wide consumer acceptance and safety profile. Finally, the convenience of being able to isolate combinations of the milk proteins together during manufacture and storage also appears to be improving overall anti-microbial effect, and early indications suggest this also improves retention of the beneficial selectivity profile.

As used herein the term "selectivity" refers to a difference in inhibitory activity towards commensal bacteria and against pathogenic bacteria and/or opportunistic pathogenic bacteria. Conveniently the level of selectivity may be represented numerically by comparing suitable quantified levels of inhibition, such as minimum inhibitory concentrations (MIC), such as MIC, $MIC_{50}$ or $MIC_{90}$ values. The comparison is typically made between two different species, but may also be made between strains within the same species. The comparison may be represented as a ratio of:

(the inhibitory activity towards a commensal bacterial species) to (the inhibitory ratio against a pathogenic bacterial species); or (the inhibitory activity towards a commensal bacterial species) to (the inhibitory ratio against an opportunistic pathogenic bacterial species).

The level of selectivity may be low, medium or high, and may be quantified as being greater than or equal to 1.1, 1.5, 2, 5, 50, 100, 200 or 300.

As used herein the terms "inhibit", "inhibition", "inhibitory", particularly with respect to bacterial growth, refer to a decrease in the rate of growth of the bacterial species with reference to the uninhibited rate of growth of the bacterial species. Typically bacterial growth can be measured by counting the change in the number of cells as a function of time, although other methods such as medium digestion, metabolite production, etc are envisaged. In some embodiments, the degree of inhibition is determined by measuring the difference in rate of growth of a population of a bacterial species as a function of time as compared to a different population of the bacterial species grown in the same conditions without the inhibitor, such as the combination of the present invention.

Preferred Features of the Combination (for Example the Cationic Fraction of Milk)

Throughout this specification, use of the term 'cationic fraction' should be taken as meaning a fraction or isolated components from a milk, being cationic components that bind to cation exchange media, and include any component of milk which has an isoelectric point of or above substantially 6.8.

Throughout this specification, the term "commensal" should be taken as meaning an organism that is normally harmless to the host, and can provide beneficial effects to the host.

The inventors found that some or all the proteins in the cationic fraction isolated from milk are collectively working together to somehow induce highly beneficial selectively towards numerous pathogenic micro-organisms without a comparative level of inhibition of commensals. Further testing is being conducted to determine which particular combination(s) provide the best results; however initial trials have indicated that selectively is synergistically enhanced if retaining more proteins from the cationic fraction of milk together.

As used herein, the term "synergistic" means that the effect achieved with the compositions and combinations of the invention is greater than the sum of the effects that result from using the individual components as a monotherapy. Advantageously, such synergy provides greater efficacy at the same doses, and provides an effect where otherwise there would be no discernible effect.

It should be understood that the particular method of combining the proteins in the composition together, which appear to provide advantageous selectivity, should not be considered to be a limitation to the invention at hand. For instance, with knowledge of the selectivity results observed herein and a clear understanding of what proteins are in the cationic fraction, a person skilled in the art could potentially prepare a combination of proteins from different sources, or even potentially synthetically engineer each protein and combine them as appropriate. However, the ability to separate and elute a cationic fraction using chromatographic methods represents a convenient way to prepare the combination(s) of the invention as a composition, and also provides a delicate mechanism to keep the proteins in their innate environment to avoid loss of protein function or inter-engagement with the other milk proteins, and to promote any form of synergism that appears to be at play between the proteins.

The proteins used in the combination, such as the composition, may be isolated or extracted from one or more sources of milk, such as bovine milk, sheep milk, goat milk, buffalo milk, camel milk, human milk and the like. The major and minor proteins found in bovine milk (used for this preliminary study) are also found in other sources of milk, with very similar isoelectric points in each case. Additionally, the term milk should be taken to include whole milk, skim milk or whey.

Therefore, based on the closely related proteins found in such milk sources, one would expect such proteins to synergistically work together in combination to provide a similar selectivity response, and could be conveniently extracted and stored together as a cationic fraction isolated from any given milk source.

In one preferred embodiment the cationic fraction may a molecular weight distribution of 3,000-80,000 Daltons by SDS-PAGE.

This protein size distribution range encompasses the size of the proteins observed within the cationic fractions (and sub-fractions) of milk.

The most prevalent proteins in the cationic fraction and proteins in preferred embodiments of the present invention are lactoferrin, angiogenin and lactoperoxidase. The relative amounts do vary a lot in milk. Typically, the cationic fraction (and therefore potentially the resulting combination, such as the composition,) may include lactoferrin in the range between 20-70% w/w and lactoperoxidase in the range between 5-40% w/w. The inventors believe these proteins may be primarily responsible for the impressive, yet unexpected selectivity towards pathogens in favour of promoting the commensals in the microbiome.

However, there also a wide number of additional proteins in milk which may be isolated as part of the cationic fractions and combinations, such as a compositions, studied by the inventors, many of which may also be contributing towards the beneficial selectivity observed across a wide number of pathogens vs commensals.

Without limitation, the proteins found in the cationic fraction of milk, and also considered to be relevant to the invention at hand, are discussed in more detail below. It should be appreciated that although many of these proteins are thought to be associated with an innate immune response and/or impart some level of biocidal activity, it has never been elucidated that the proteins from milk may work together synergistically to provide selectivity towards micro-organisms to help modulate a microbiome environment.

Lactoperoxidase

Lactoperoxidase (Lp) is a protein present in the mammary gland secretion and many other exocrine secretions of mammals.

The Lactoperoxidase system consists of three components—Lp, thiocyanate and hydrogen peroxide, which are all present in fresh milk. Lp catalyses the oxidation of thiocyanate by peroxide and generates intermediate products (hypothiocyanite ($OSCN^-$)), with antibacterial properties. Thiocyanate is present in the mammary, salivary and thyroid glands and their secretions, in synovial, cerebral, cervical and spinal fluids, in lymph and plasma, and in organs such as stomach and kidney. Hydrogen peroxide, the third component of the Lactoperoxidase system is not normally detected in milk, but is present during infection.

The Lactoperoxidase system has bacteriostatic or bactericidal activity on a variety of susceptible micro-organisms including bacteria, fungi and viruses associated with mastitis.

The inventors previously identified through a major R&D product pre-2006 (the subject of NZ Patent 547849) that the cationic fraction, which includes lactoperoxidase and other preferred proteins isolated from milk, was able to be used effectively to treat mastitis by attacking the causative micro-organisms in the mammary gland after administration. This major breakthrough over 10 years ago was important because it provided a treatment which cleverly engaged from the innate immune response of the mammalian mammary gland environment, and utilised endogenously found proteins produced by the actual mammary gland. Furthermore, the composition's efficacy did not rely on conventional antibiotic treatment, which in the dairy industry was an important feat as it avoided issues with increased antibiotic resistance, long withholding periods and addressed a growing consumer desire for natural alternatives to antibiotic treatments. The inventors also envisaged at the time that the same composition would also be useful to treat infections on other areas on the body besides mastitis.

However, the inventors have now only recently identified the proteins found in this cationic fraction have an important further therapeutic and commercial characteristic, that being high selectivity toward pathogenic micro-organisms yet with a dramatic low inhibition of beneficial commensals. This opens up an entirely new application of the milk proteins to improve microbiomes present on or in the body of humans or other animals.

Furthermore, it overcomes the problems associated with administering antibiotics which are not selective towards pathogens, and therefore destroys the entire microbiome, including both pathogens and commensals. Prebiotics or probiotics act to more conservatively boost the commensals but without any direct inhibitive function. However, the present invention has a direct inhibition effect on pathogens, making it a more potent tool to combat infections, or conditions which have a poorly functioning microbiome overridden with pathogenic micro-organisms.

In fact, this newly discovered selectivity opens the door to potentially combining the selectively antimicrobial milk-derived components with prebiotics or probiotics in order to further enhance the balance of the native microbiome, whilst simultaneously exogenously adding to the natural commensal activity. This is a functional advantage of the present invention that would not otherwise have been possible with prebiotics or probiotics alone.

Quite contrary to the present invention, U.S. Pat. No. 5,888,505 describes that different forms of peroxidase have a wide variety and specificity towards targeting pathogenic micro-organisms. The results suggested that lactoperoxidase was effectively providing no or very little selectivity between the different micro-organisms compared to the other forms of peroxidases. Contrary to this, the inventors have now discovered that the cationic fraction in milk, which relies exclusively on lactoperoxidase action (instead of other peroxide forms) yet together with other protein(s) isolated from milk with a pI above 6.8, performs remarkably well, and in fact appears to significantly outperform the specificity and broad spectrum effectiveness seen in U.S. Pat. No. 5,888,505. Furthermore, the present invention does not require peroxide or halide addition for therapeutic effectiveness (although either may be included if the treatment site is devoid of natural substrates like peroxide/halide), and does not require high concentrations of lactoperoxidase in order to achieve a desirable knockdown effect. Additionally, there is reasonably good consumer acceptance of lactoperoxidase in commercial products. Further to this, milk proteins are stable and can be sourced cheaply.

U.S. Pat. No. 6,544,498 discloses the extraction by gradient elution of a basic protein fraction which has an isoelectric point between 7.5 and 11 and a molecular weight distribution of 3,000 to 80,000 Daltons, with the main components being lactoperoxidase and lactoferrin. U.S. Pat. No. 6,544,498 argues that the inventiveness of their application is based on the fraction curbing the decrease in alveolar bone and shows experimental data supporting this. There is no indication that the composition in U.S. Pat. No. 6,544,498 was identified to have selectivity towards pathogenic bacteria without a similar inhibition towards commensals, nor was there any discussion that selectivity could be enhanced dramatically by combining many, if not all, of the suite of proteins as described in the present invention with milk proteins with a pI above 6.8. In fact a number of subsequent publications confirm that the protein fraction in U.S. Pat. No. 6,544,498 acts to curb the decrease in alveolar bone by promoting osteoblast proliferation (see for example: U.S. Pat. No. 8,647,619; Aoe, S., et al. A controlled trial of the effect of milk basic protein (MBP) supplementation on bone metabolism in healthy menopausal women. *Osteoporosis International* 2005; 16:2123-8; Yamamura, J., et al. Milk basic protein (MBP) increases radial bone mineral density in healthy adult women. *Bioscience, Biotechnology, and Biochemistry* 2002; 66(3):702-4; Dorit Naot; Andrew Grey; Ian R. Reid; Jillian Cornish Lactoferrin—A Novel Bone Growth Factor Clin Med Res. 2005 May; 3(2): 93-101) rather than by any antibacterial activity, let alone selective antibacterial activity. Therefore, U.S. Pat. No. 6,544,498 does not teach towards the invention.

Lactoferrin

Lactoferrin (Lf) is a glycoprotein which is present in mammary gland secretion and many other exocrine secretions of mammals. Lf is secreted predominately by surface epithelia into the mucosal environment. Lactoferrin is a multifunctional protein that has antibacterial, antifungal, antiviral, antitumour, anti-inflammatory, and immunoregulatory properties. Therefore, the inventors expect that Lactoferrin is contributing to the anti-microbial effects of the combination, such as the composition, but more importantly is somehow, in combination with the other protein(s) in the combination, helping to impart an intricate level of selectivity towards pathogenic micro-organisms yet with very low MIC levels towards commensals.

Lf is produced at high levels in nasal and tracheal passages, and in gastric, genital and ophthalmic secretions. Lf is also produced at high levels in neutrophils where it is stored in secondary granules and released during inflammation.

The mechanism by which Lf inhibits microbial growth has not been fully elucidated. Its antimicrobial and anti-inflammatory effects are believed to be as a result of a number of different actions or functions of Lf.

The highly basic N terminal region of bovine lactoferrin is thought to be essential for antimicrobial activity. The 25 N-terminal amino acids may be removed by proteases to form lactoferricin (Lfcin). These proteases may be naturally occurring in milk or serum, and many micro-organisms produce proteases. Lfcin is up to a 1000 fold more effective against some micro-organisms than intact lactoferrin. Lfcin has been shown to inhibit a diverse range of microorganisms such as gram-negative bacteria, gram-positive bacteria, yeast, filamentous fungi, and parasitic protozoa, including some antibiotic-resistant pathogens. Therefore, it is plausible that lactoferricin may be added to the combination, such as the composition, replace lactoferrin, and/or be a natural degradation product of lactoferrin in the combination of the present invention due to proteolytic action.

Lf binds to lipopolysaccharide. When Gram-negative bacteria are killed by the natural defense system of the animal or by antimicrobial agents the release of lipopolysaccharide from the cell walls of the bacteria provokes an inflammatory response. One of the primary actions of Lf therefore is to bind the LPS and prevent the inflammatory response. Lf also displays an immunomodulatory role by binding with high affinity to bacterial endotoxin, thus protecting against endotoxin lethal shock.

Lf is also an iron binding glycoprotein. Most micro-organisms need iron for growth and therefore Lf has the potential to inhibit the growth of bacteria and even kill them by depriving them of iron. The effectiveness of the antibacterial activity of Lf depends on the iron requirement of the organism, availability of exogenous iron, and the concentration and degree of iron saturation of Lf.

Current commercial applications of bovine Lf include infant formulas, fermented milks, nutritional iron supplements, chewing gums, immune-enhancing nutraceuticals, cosmetic formulas and feed and pet care supplements. Therefore, it is advantageous to note that there is general consumer acceptance, and food safety regulations for use of Lactoferrin in the combination, such as the composition.

Angiogenin-Ribonuclease

Angiogenin-Ribonuclease belongs to the ribonuclease superfamily have been identified in milk, and is known to have some anti-viral and anti-microbial activity. Therefore, the inventors expect that Angiogenin-Ribonuclease is contributing to the anti-microbial effects of the combination, but more importantly is somehow (in combination with the other protein(s) in the combination) helping to impart an intricate level of selectivity towards pathogenic micro-organisms yet with very low MIC levels towards commensals.

Lysozyme-Like Proteins, Such as Chitinase-Like Protein (CLP-1) or Lysosomal Alpha Mannosidase (LAM)

The combination preferably includes lysozyme-like protein, such as chitinase-like protein (CLP-1) or lysosomal alpha mannosidase (LAM). Lysozyme-like proteins (such as CLP-1 or LAM) have cell lysing activity and thereby are thought to enhance antimicrobial activity through their lysozyme-like effects.

In a preferred embodiment, the combination (such as the cationic fraction) may also include quiescin and/or jacalin-like protein.

Other milk proteins that may be included within the combination to improve its effectiveness (either through imparting selectivity, or some other form of indirectly modulation of the protein(s) functionality) include:

cathelicidin 1;
N-acetyl glucosaminidase;
serum amyloid A;
β Defensin;
Peptidoglycan recognition protein;
Xanthine dehydrogenase;
Immunoglobulin(s) IgA, IgD, IgG, IgM, IgA, and/or IgE;
Growth factors EGF, IGF 1, TGF B1 and TGF B2.

Immunoglobulins are important components of milk and provide passive protection to the suckling young. Although they are not strongly cationic some immunoglobulins, IgG, IgM, IgA and polymeric immunoglobulin receptor (PIGR) are captured by cation exchange. Immunoglobulins are important in the first line of defense against foreign invaders. Immunoglobulins bind to micro-organisms and thus opsonise them so that they are more easily recognized by phagocytic cells. It is plausible, therefore, that they may also have some effect on the observed selectivity in the present invention, and may be working synergistically with other proteins in the cationic fraction.

It is anticipated that the combination (such as the cationic fraction) isolated from milk may also include small amounts of a number of growth factors; although these growth factors may be present at low levels, their action can be potent in stimulating cell repair. These growth factors may include for example: EGF, IGF 1, TGF B1 and TGF B2.

Interestingly, Smolenski et al. (2007) reported on the identity and significant number of minor proteins in bovine milk by Mass Spectrometry (MS) and, in particular, identified a significant number of milk proteins that are involved in host defense. Yet, Smolenski in no way mentions or suggests any selectivity for any of the individual proteins, or combination of proteins despite mentioning that individual proteins have anti-microbial activity. The results are shown in Table 1, which we have adapted to show, in bold, some of the proteins which correspond to those preferably incorporated into the combination of the present invention (and which were isolated via the cationic fraction in milk and shown to have high selectivity according to the present invention). It should be noted that Smolenski et al. (2007) used SDS-PAGE methods that do not disclose the detection of the proteins identified in the combinations (such as compositions including the cationic fraction) used in the present invention (e.g. angiogenin, jacalin-like protein, quiescin, PIGR and the growth factors).

Table 1. Host defense-related minor proteins identified from milk, showing some of those that may be extracted as part of the cationic fraction (bold) (reproduced from Smolenski et al., 2007)

TABLE 1

Minor proteins identified in bovine milk.

| ACC Number | Protein Name | Function | pI |
|---|---|---|---|
| NP_777250 | cathelicidin 1 (Bactenecin 1) | antimicrobial properties | 6.8* |
| AAB64304 | chitinase-like protein 1 (CLP-1) | eosinophil chemotactic properties | 8.8 |
| Q290092 | endoplasmin precursor (GRP94/GP96) | participates in the assembly of antibody molecules and signaling molecule for polymorphonuclear neutrophils | 4.7 |
| NP_776758 | glucose regulated protein 58 kDa | regulates signaling by interacting with stat3 | unknown |
| NP_776770 | heat shock 70 kDa protein 8 | activated through proinflammatory response mechanisms enhancing MMP-9 expression in monocytic cells | 5.4 |
| NP_071705 | heat shock 70 kDa protein 5 (glucose-regulated protein) | upregulation in macrophages upon IL-4 stimulation | unknown |
| AAA18337 | heat shock protein 27 | inhibitor of neutrophil apoptosis | 5.98* |
| BAA32525 | heat shock protein 70 kDa protein 1A | stress response (refolding and degradation of denatured proteins) | 5.68* |
| AAC98391 | immunoglobulin IgA | antigen recognition | X¹ |
| AAN07166 | immunoglobulin IgD | antigen recognition | X¹ |
| AAB37381 | immunoglobulin IgG | antigen recognition | X¹ |
| AAN60017 | immunoglobulin IgM | antigen recognition | X¹ |
| AAQ88452 | IRTA2 | B-cell immunoglobulin super-family receptor | unknown |
| AAA30617 | lactoferrin | iron binding and antimicrobial peptide "lactoferricin" | 8.67* |
| NP_776358 | lactoperoxidase | oxidative peroxidase activity | 8.327* |
| BAA07085 | lymphocyte cytosolic protein 1 (65K macrophage protein/L-plastin) | regulation of neutrophil integrin function | 5.21* |
| P21758 | macrophage scavenger | mediate the binding, internalization and processing of negatively charged macromolecules | 5.7* |
| AAA36383 | nucleobindin 1 | promotes production of DNA-specific antibodies | 5.05* |
| NP_776998 | peptidoglycan recognition protein | innate immunity pattern recognition molecule | 9.38* |
| XP_611685 | S100 calcium binding protein A9 (calgranulin B) | associated with S100A8 and implicated in inflammatory response | 6.29* |
| XP_593653 | S100 calcium binding protein A11 (calgizzarin) | upregulation associated with proinflammatory response | 6.7 |
| NP_777076 | S100 calcium binding protein A11 (calgranulin C) | antimicrobial peptide "calcitermin" | 5.9 |
| P42819 | serum amyloid A protein | involved in acute phase cytokine signaling | 6.94 |
| CAA67117 | xanthine dehydrogenase | superoxide anion, hydrogen oxide and peroxynitrite production | 8.0 |

¹Immunoglobulins typically have isoelectric points the range of 5.0-9.5. As such, not all bind to the cationic exchange resin.
*The isoelectric points of these proteins have been calculated based on the expected protein structure. (Swiss Prot/TrEMBL, www.expasy.org).

Some of the cationic fraction components (e.g lactoferrin, angiogenin) may also have minor variants, —such as variations in amino acid sequence or in degree and type of glycosylation, these minor variants, and their presence in the cationic fraction should also be taken as being covered by the present application.

In one preferred embodiment the final treatment combination, such as the composition, may be in the form of a liquid, cream, gel, paste, powder, capsule, lozenge, tablet, suppository, bolus, injectable solution and so forth.

The final treatment combination may include at least one or more of the following: carriers, buffers, preservatives, excipients or other pharmaceutically acceptable components required to ensure the cationic fraction is in a form that is easily dispensed, used and is efficient for the purpose of selectively supporting the microbiome.

In one embodiment the final treatment combination may also include at least one component which is capable of controlling the time release of the combination. This may be used to effectively to extend the release of the therapeutic effect over an extended period of time. Known components which could be used for this purpose would be well known to one skilled in the art.

The combination, such as the composition, may also include one or more of the following:

1. a peroxidase substrate,
2. hydrogen peroxide or a source of hydrogen peroxide;
3. a cell-lysing substance capable of fully, or partially lysing cell walls (such as detergents like monoglyceride or monolauryl glycerol [monolaurin]).

The peroxidase substrate may be any substrate or compound on which lactoperoxidase or any other peroxidase enzymes may act. In one preferred embodiment the peroxidase substrate may be thiocyanate.

In one particular preferred embodiment the peroxidase substrate may be potassium or sodium thiocyanate. Alternatively any other thiocyanate which can act as a peroxidase substrate may be utilized.

In a preferred embodiment the minimum concentration of peroxidase substrate is 20 ppm (when the peroxidase substrate is sodium thiocyanate), 20 ppm (when the source of hydrogen peroxide is ascorbate) and 5 ppm (when the cell lysing agent is monolauryl glycerol) (as shown in vitro).

However, one skilled in the art would realize that these may differ depending on the type of combination being applied, i.e. a liquid or a paste and the specific site of application or action.

One skilled in the art would also realize that in vivo, the site of application may already have peroxidase substrate present. In this case it may not be required to be included in the formulation, or may be able to be included at a lower concentration.

In a preferred embodiment the source of hydrogen peroxide used may be ascorbate or ascorbic acid.

Ascorbate and ascorbic acid have been shown in previous publications to be good substrates for peroxidase enzymes. This is a preferred source of hydrogen peroxide as it is stable—unlike peroxide itself.

Hydrogen peroxide is also a substrate of peroxidase enzymes. Therefore, one skilled in the art would realize that the same considerations would apply as discussed above in relation to the peroxidase substrate.

Therapeutic Uses

Although the trial results will be outlined in greater detail in the Best Modes section, we briefly outline some pathogens and commensals that are known to be present in microbiomes and therefore may be targets of the invention. Further below, we outline therapeutic areas of the body, together with potential conditions/diseases which may benefit as a result of this newly identified selectivity and modulation of microbiomes.

Preferably (yet without limitation), the pathogenic and/or commensal micro-organisms are selected from the group consisting of gram-positive bacteria, gram-negative bacteria, aerobic bacteria, anaerobic bacteria, fungi, yeasts and/or viruses. Initial results illustrate that there will be a wide selectivity towards pathogens in many, if not all, of these different organism types.

Initial trials (the results of which are shown in Table 4) have shown clear selectivity (a low MIC between 0.1 and 0.5) that may be required to inhibit a wide selection of pathogenic micro-organisms (or which can become pathogenic if the microbiome is compromised) including *Propionibacterium acnes, Streptococcus pyogenes, Candida albicans, Trichophyton mentagrophytes, Trichophyton rubrum, Malazzezia furfur, Escherichia coli*. These pathogenic micro-organisms are implicated in infections on the skin, hair, nails, gut, nose, ears mouth, vagina, anterior urethra, lungs and any other areas of the body that has a surface that is either accessible to external gases, liquids, foods, etc. or is isolated from internal systems via a blood barrier, such as the mammary gland, which exemplifies the broad therapeutic uses of the combination. Further trials are being conducted to determine other targets, with the expectation of success.

In conjunction, the initial trials conducted by the inventors have shown that the combinations show a comparatively low level of inhibition across a wide range of commensal micro-organisms, which are outlined in greater detail in the Best Modes section. For instance, the MIC (mg/ml) for commensal micro-organisms is 20-100 fold (Table 4) higher compared to the MIC for most pathogens. This means the combination has low inhibitory effectiveness towards commensals, such that they can proliferate and populate the microbiome, whilst the pathogens at the site of infection are attacked by the combination.

The inventors also expect that the combination may have the ability to selectively modulate opportunistic commensals, which although imparting benefits to the host in a healthy environment, may cause infection or harm if the microbiome is either weakened, or if the commensal enters through a barrier such as the skin or gastrointestinal lining, for instance due to an injury. In such a case, the commensal may become pathogenic, and the combination may have the ability to selectively modulate the microbiome, thereby lessening the chance of or the severity of the infection. There are many examples of commensals which may become opportunistic, and there is considerable research into this area to understand the complexity of this aspect of the microbiome environment.

It should be appreciated that the invention should not be limited to just the micro-organisms tested during preliminary trials, as it is expected the selectivity will have far reaching outcomes with many therapeutic uses. The broad specificity trend across a wide range of pathogens vs commensals means the same combination may be advantageously utilised to treat a wide range of conditions, and/or be administered to provide a preventative or boosting effect to support healthy microbiomes in a wide range of areas on or in the body.

This advantage is even further enhanced by the fact that the combination may rely essentially on endogenous proteins found in nature which can be extracted from milk which has wide consumer acceptance.

The synergistic therapeutic effectiveness of the proteins in combination (emphasised by comparison to the results in U.S. Pat. No. 5,888,505) is also cleverly making use of the easy ability to isolate the proteins together in a delicate manner to preserve their native interactions with other proteins, and to preserve stability of the combination before consumption.

Areas to be Treated

As will be readily appreciated by those skilled in the art, the route of administration and the nature of the pharmaceutically acceptable carrier will depend on the nature of the condition and the animal (preferably mammal) to be treated. It is believed that the choice of a particular carrier or delivery system, and route of administration could be readily determined by a person skilled in the art.

The combination of the invention may allow for separate, sequential or simultaneous administration of the lactoperoxidase and the at least one other component extract as hereinbefore described. The combination may be provided in the form of a pharmaceutical composition, in which the lactoperoxidase and the at least one other component are in intimate admixture.

Typically a therapeutically effective amount of the combination of the invention will be administered. The term "therapeutically effective amount" refers to that amount which is sufficient to effect treatment, as defined below, when administered to an animal, preferably a mammal, more preferably a human in need of such treatment. The therapeutically effective amount will vary depending on the subject and nature of the disease being treated, the severity of the infection and the manner of administration, and may be determined routinely by one of ordinary skill in the art.

The terms "treatment" and "treating" as used herein cover any treatment of an infection in an animal, preferably a human, and includes: (i) inhibiting the infection; (ii) relieving the infection; or (iii) relieving the conditions caused by the infection, eg symptoms of the infection.

The terms "prevention" and "preventing" as used herein cover the prevention or prophylaxis of an infection in an animal, preferably a human and includes preventing the infection from occurring in a subject which may be predisposed to the infection but has not yet been diagnosed with the infection.

In some embodiments the combination of the present invention is formulated for topical administration. Preferably, the combination of the invention will be applied topically such as in a paste, cream, lotion, gel or via an impregnated dressing or impregnated mask. The term "topical", as used herein, refers to a combination meant for application to the skin, nail, or mucosal tissue (such as gum). The combination of the present invention is believed to be particularly effective in the treatment and/or prevention of a range of skin, nail and mucosal infections.

Without limitation, the table below (Table 2) outlines potential areas surfaces of the human body that may be treated with the combination to selectively modulate the microbiome. This may be beneficial to treat an existing infection (or disease or condition associated with said infection), or may be instead used as a preventative measure much like pre-biotics or pro-biotics to beneficially strengthen the microbiome from future infection.

For example, this information suggests using the combination to target infections in a wide number of locations, and to promote beneficial commensals whilst inhibiting or killing pathogenic micro-organisms.

Combination Products

The applicant envisages that the combination of the present invention may include other compounds or material which is known or thought to promote or enhance the microbiome. For instance, the combination may include prebiotics or probiotics. It is possible this may enhance the selectivity profiles even further.

Methods of Manufacture and Storage

Interestingly, the applicant discovered in previous studies that the inhibitory effects against the pathogen *Streptococcus uberis* (in the context of mastitis) diminished as the cationic bioactive fractions became more purified. This was contrary to common thinking as it is commonly understood that the purer a component is, the more effective it will be. At the time, this led to the hypothesis, which was subsequently tested that the 'total cationic fraction' of the present invention could be used as a successful naturally-derived inhibitory product. Additionally, previous research from this Applicant found that a combination of milk proteins (i.e. the cationic milk fraction with a pI above 6.8) induces a powerful anti-inflammatory action. Yet, it was not envisaged that this phenomenon would also have implications for

TABLE 2

Bacteria commonly found on the surfaces of the human body.

| BACTERIUM | Skin | Conjunctiva | Nose | Pharynx | Mouth | Lower GI | Ant. urethra | Vagina |
|---|---|---|---|---|---|---|---|---|
| Staphylococcus epidermidis | ++ | + | ++ | ++ | ++ | + | ++ | ++ |
| Staphylococcus aureus* | + | +/− | + | + | + | ++ | +/− | + |
| Streptococcus mitis | | | | + | ++ | +/− | + | + |
| Streptococcus salivarius | | | | ++ | ++ | | | |
| Streptococcus mutans* | | | | + | ++ | | | |
| Enterococcus faecalis* | | | | +/− | + | ++ | + | + |
| Streptococcus pneumoniae* | | +/− | +/− | + | + | | | +/− |
| Streptococcus pyogenes* | +/− | +/− | | + | + | +/− | | +/− |
| Neisseria sp. | | + | + | ++ | + | | + | + |
| Neisseria meningitidis* | | | + | ++ | + | | | + |
| Enterobacteriaceae* | | +/− | +/− | +/− | + | ++ | + | + |
| Proteus sp. | | +/− | + | + | + | + | + | + |
| Pseudomonas aeruginosa* | | | +/− | +/− | | + | +/− | |
| Haemophilus influenzae* | | +/− | + | + | + | | | |
| Bacteroides sp.* | | | | | | ++ | + | +/− |
| Bifidobacterium bifidum | | | | | | ++ | | |
| Lactobacillus sp. | | | | + | ++ | ++ | | ++ |
| Clostridium sp.* | | | | | +/− | ++ | | |
| Clostridium tetani | | | | | | +/− | | |
| Corynebacteria | ++ | + | ++ | + | + | + | + | + |
| Mycobacteria | + | | +/− | +/− | | + | + | |
| Actinomycetes | | | | + | + | | | |
| Spirochetes | | | | + | ++ | ++ | | |
| Mycoplasmas | | | | + | + | + | +/− | + |

++ = nearly 100 percent
+ = common (about 25 percent)
+/− = rare (less than 5%)
* = potential pathogen The predominant bacterial flora of humans are shown in Table 2. This table lists only a fraction of the total bacterial species that occur as normal flora of humans. A recent experiment that used 16S RNA probes to survey the diversity of bacteria in dental plaque revealed that only one percent of the total species found have ever been cultivated. Similar observations have been made with the intestinal flora. Also, this table does not indicate the relative number or concentration of bacteria at a particular site.

beneficial selectivity towards pathogenic micro-organisms vs commensals, which has only now been discovered, and which opens up a whole new set of therapeutic uses.

It should be appreciated that the term milk may include any raw (or unprocessed) milk. This is taken to include raw milk which has been chilled, incubated, or stored, at either a chilled or ambient temperature.

In one preferred embodiment the cationic fraction may be extracted from bovine milk.

However, this should not be seen as limiting, as the cationic fraction may also be extracted from other mammalian species, including, but not limited to sheep, goats, buffalo, camels and humans.

In one embodiment the proportions of the different cationic components within the cationic fraction may be as extracted, or concentrated.

However, this should not be seen as limiting, as it may be desirable to alter or control the ratio of at least one, or a number of components respectively. It should be appreciated that any such alteration in the proportions of the cationic fraction components are covered by this disclosure.

In one preferred embodiment the cationic fraction may be extracted "on-farm", during or directly after the milking process. This may be advantageous as some of the components may be lost, damaged or denatured during subsequent handling, storage, fat removal, or other processing steps.

Many methods may be used to prepare a combination, such as a composition, as described according to the present invention. However, cationic exchange is considered to be a preferred method of manufacture, as will discussed in further detail below and exemplified in the Best Modes.

Preferably, the method includes extracting preferred proteins from milk, including the steps of:
a) passing milk through an extraction material, and
b) eluting a cationic fraction of the bound milk components having a pI above 6.8.

In a preferred embodiment the extraction material may be a cation exchange material. This may either be in the form of resin, expanded bed resin, magnetic beads, membrane or other suitable form for large scale extraction.

In a preferred embodiment the cation exchange material may be any material that has sufficient mechanical strength to resist high pressures and maintain high flow rates.

In a preferred embodiment the cation exchange resin may have a mean particle size in excess of 100 μm. Resins in larger bead form have been developed for use with viscous feed streams because they do not pack as closely as smaller beads therefore there are wider channels so that there is not excessive back-pressure.

Examples of suitable cation exchange resins are SP-Sepharose Big Beads, SP-Sepharose Fast Flow, SP-Toyopearl and S-Ceramic HyperD.

One example of an extraction and purification process is as follows:

Lactoferrin binds firmly to cation exchange and is the last major protein to elute in a salt gradient. Therefore a single step elution with 1M salt (80 mS-100 mS) elutes all proteins and peptides in a single fraction (cationic fraction). Elution with 80-100 mS salt following a prior 40 mS elution will yield a fraction that is primarily lactoferrin.

After lactoferrin, lactoperoxidase is the next most abundant of the cationic proteins captured by ion exchange from milk (0.03-0.075 mg/ml milk). In a salt gradient lactoperoxidase elutes from cation exchange before lactoferrin at 25-30 mS.

The growth factors EGF, IGF 1, IGF 2, TGF B1 and TGF B2 are present in milk in ng/ml quantities, and have been shown to be captured by cation exchange.

A number of other biologically active cationic peptides elute between lactoperoxidase and lactoferrin at 35-40 mS (intermediate fraction). These are likely to include quiescin, jacalin-like protein, and lysozyme-like proteins, such as chitinase-like protein (CLP-1) or lysosomal alpha mannosidase (LAM). Therefore the concentration of salt used at each step in the elution determines whether these biologically active peptides are in the lactoperoxidase fraction or the lactoferrin fraction. In preliminary studies, the inventors have identified that the whole cationic fraction appears to have a much higher level of selectivity compared to just proteins in the intermediate fraction.

Immunoglobulins are eluted in low salt (15-20 mS).

In a preferred embodiment the milk, or milk product may be passed through a membrane having cationic exchange properties, or a column packed with the cationic exchange resin or a batch reactor with suspended cationic resin, whereby the micro-components adsorb from the starting milk or product thereof onto the cationic exchange resin or membrane.

After adsorption of milk micro-components the cationic fraction is preferably extracted by elution with a salt solution.

However, this should not be seen as limiting as elution of the cationic fraction may also be via a shift in pH. This method, however, is not popular in large scale commercial processes as the high pH required to remove lactoferrin from the resin could be damaging to the lactoferrin, or in the present case any other components in the cationic fraction.

In a preferred embodiment, before elution, the resin or membrane may be rinsed with a salt solution. Preferably the rinse solution may be sodium chloride or sodium bicarbonate, with conductivity between 5 and 10 mS (millisiemens/cm). This rinse step ensures that substantially all non-adsorbed milk components are rinsed off the resin or out of the membrane.

In a preferred embodiment the cationic fraction may be eluted in a salt gradient between substantially 10 mS and 100 mS conductivity (0.1 to 2.0 M salt).

In a preferred embodiment the cationic fraction may be eluted in a single fraction by passing a salt solution with conductivity between 80 and 100 mS through the column or membrane.

In a preferred embodiment the elution salt may preferably be sodium chloride. However, this should not be seen as limiting as other salts including sodium acetate, sodium bicarbonate, ammonium bicarbonate, or potassium chloride may be used.

Having the cationic fraction eluted in a one-step elution provides a significant advantage. It decreases the length of extraction time thereby decreasing the possibility of bioactives being denatured. It also decreases the time, labour and cost of the extraction process. This can provide a significant advantage, especially on a large scale. Furthermore, the results clearly show that inhibitory effect (and we also expect selectivity) will be enhanced when the components of milk having a pI above 6.8 are retained as a single isolated fraction and administered together.

In a preferred embodiment after initial monitoring of the protein levels in the eluted stream to determine the concentration of salt and the volumes required to elute all the protein, the typical large scale process operates on volumes rather than continuous monitoring.

In a preferred embodiment the extraction may be undertaken in a continuous manner.

In another preferred embodiment, the extraction may be undertaken in a batch elution.

In the above preferred embodiments the cationic fraction may be extracted by a 'one-step' process, by step elution.

In an alternative embodiment the cationic fraction may be extracted using a gradient elution.

However this should not be seen as limiting as the cationic fraction may also be extracted in independent fractions and recombined to form the complete cationic fraction at a later stage.

In some embodiments the cationic fraction may undergo further treatments, by standard techniques known in the art, for example, to remove salt, or to concentrate, or to filter for sterility or to remove endotoxin. The concentrated fraction may also be lyophilised.

In a preferred embodiment the cationic fraction may be concentrated to approximately 20% solids.

In the case of the cationic fraction being extracted from milk that is processed in the usual manner involving storage, transport and conversion to skim milk or whey the temperature should preferably be maintained at substantially 4-7° C. to minimize microbial growth.

In the case of the cationic fraction being extracted from whole milk the temperature should preferably be maintained at not less than 35° C. to ensure that lipids remain in a liquid state so that they can easily pass through the extraction material. And to ensure the bioactivity of the factors in the cationic fraction are maintained at or close to the endogenous state.

In an alternative embodiment the cationic fraction may be extracted from genetically modified animals, for example genetically modified enhancement of lactoferrin production in dairy cows. One skilled in the art would realise that extraction from the milk of genetically modified animals may affect the ratio or concentrations of lactoferrin, or other components in the cationic fraction, or a whole cascade of key components.

In one preferred embodiment the cationic fraction may be extracted from the same species of animal that the treatment substance is intended to be used on.

Summary of Advantages

The present invention is believed to provide a number of significant advantages including:
  High selectivity towards inhibition of a wide number of pathogenic micro-organisms without a similar level of inhibition towards a wide number of commensals;
  Potential for ability of combination, such as the composition, to target opportunistic commensals;
  Likelihood of further synergies with other components such as pre-biotics or probiotics;
  Low concentration of lactoperoxidase in the combination needed to achieve desired effect, so as to avoid likelihood of issues such as hemolysis.
  The synergy observed towards improved selectivity appears to be closely linked to the retention of lactoperoxidase together with other protein(s) in the cationic fraction of milk with a pI above 6.8, which also conveniently is beneficial in terms of ease of manufacture, improved stability, and consumer acceptance (low processing required). This is contrary to U.S. Pat. No. 5,888,505 which highlighted purified forms of peroxide (e.g. myeloperoxidase) together with added halides/cofactors are needed to achieve a desired result, and further that lactoperoxidase essentially had no ability to provide selectivity between pathogens and commensals.

The ability to provide a cationic fraction eluted in a one-step elution decreases the length of extraction time required for extraction, thereby decreasing the possibility of bioactives being denatured. It also decreases the time, labour and cost of the extraction process. This can provide a significant advantage, especially on a large scale. It also appears to improve inhibitory effects, and we expect retention of the selectivity profiles.

The combination, such as the composition, may be prepared conveniently from milk and is therefore considered to be natural and safe to use.

Unlike broad spectrum antibiotics (which will kill all the micro-organisms in the microbiome), the cationic fraction naturally preserves the beneficial commensals.

Unlike probiotics or prebiotics, the combination is potent at inhibiting pathogenic micro-organisms and therefore will have a better therapeutic effect for treating existing infections (not just being a preventative).

Equally, the potency of the combination does not rule out the ability to use the combination in a preventative manner to boost, modulate or maintain a person's (or other animal's) microbiome to avoid infections, conditions or diseases from transpiring in future.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Figure 1:
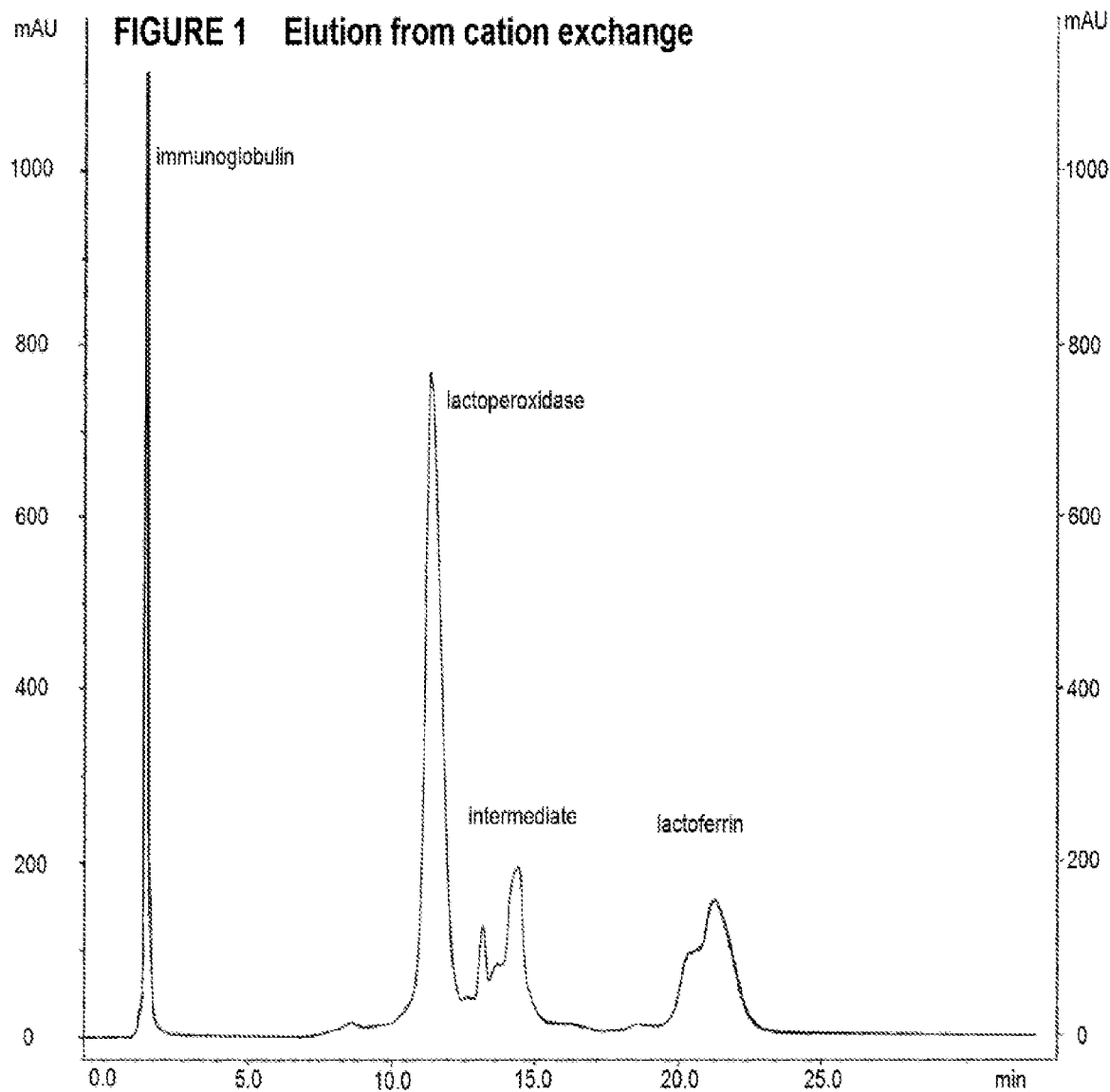
FIG. 1 shows the general elution profile of all the fractions from cation exchange. This represents all the protein peaks (as detected at 280 nm) that would be present in a single fraction eluted in a gradient from 80-100 mS. The main components in the cationic fraction are immunoglobulin, lactoperoxidase, lactoferrin, and a group of minor components that include angiogenin.
Figure 2:
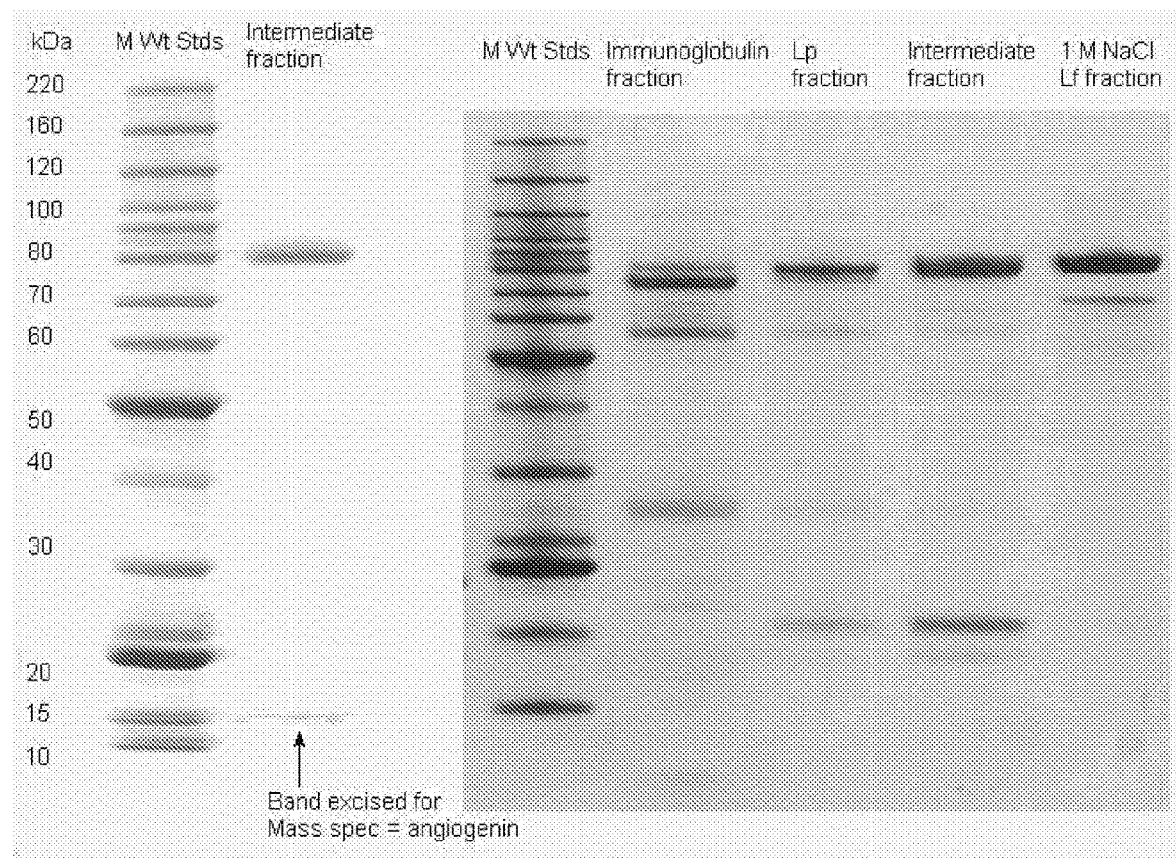
FIG. 2 shows the fractions separated on SDS-PAGE, and indicates the band that was excised for Mass Spectroscopy and identified as bovine angiogenin. The immunoglobulin fraction shows PIGR (76 kDa) as the predominant band, and the heavy (52 kDa) and light chains of immunoglobulin. The Lp fraction is mainly lactoperoxidase with a small amounts of heavy and light chains of immunoglobulin and angiogenin. The intermediate fraction has a prominent band of lactoperoxidase and lactoferrin (80 kDa) and a band at around 15 kDa that was identified by Mass Spectrometry as angiogenin, a band at approximately 13 kDa that was identified by Mass Spectrometry as jacalin-like. The Lf fraction is predominantly lactoferrin (80 kDa).

Example 1: Assessment of the Proteins in the Composition (i.e. the Cationic Fraction) Via Mass Spectrometry The process of producing the cationic fraction involved fractionating milk through a cation exchange resin, eluting the bound components from the resin using a salt solution, which can be either a one-step high molarity (>1M) salt or a gradient elution from a lower molarity up to over 1M, collecting the eluted components in a single fraction, and then desalting and purifying the collected fraction.

The cationic fraction was analysed for its constituent components, and the results shown in Table 3. This shows a typical result for yield and identity of the major proteins identified in the cationic protein fraction.

This particular cationic fraction was captured from raw, whole milk.

TABLE 3

Sub-fractions from the cationic fraction, as measured by Mass Spectrometry (MS). (Lactoperoxidase was determined via extinction coefficient rather than MS.)

| Identity from MS | Total Protein (mg/ml) | % of total | Isoelectric point |
| --- | --- | --- | --- |
| lactoperoxidase | 4.2 | 8.0% | 8.3 |
| quiescin | 1.6 | 3.0% | 8.69 |
| jacalin-like protein | 1.4 | 2.7% | 8.71 |
| chitinase-like protein | 0.4 | 0.8% | 8.74 |
| angiogenin | 10.0 | 19.0% | 9 |
| Lactoferrin | 35.0 | 66.5% | 8.7 |
| TOTAL | 52.6 | 100.0% | |

Example 2: Inhibition Trials on Pathogens Vs Commensals

The Applicant used the methodology described herein to prepare a cationic fraction isolated from bovine milk as described in Table 3. The composition was tested in vitro against a number of micro-organisms using micro-titre plates and some in agar diffusion tests. The results are shown in Table 4 (shown below) identify the MIC (mg/ml) of the cationic fraction against the different micro-organisms.

TABLE 4

Inibitory analysis of cationic fraction against range of commensals and pathogens.

| | MIC mg/ml |
| --- | --- |
| Pathogens | |
| Propionibacterium acnes | 0.1 |
| Trichophyton mentagrophytes | 0.1 |
| Trichophyton rubrum | 0.1 |
| Escherichia coli | 0.1 |
| Streptococcus pyogenes | 0.1 |
| Malassezia furfur | 0.2 |

TABLE 4-continued

Inibitory analysis of cationic fraction against range of commensals and pathogens.

| | MIC mg/ml |
| --- | --- |
| Commensal/Opportunistic pathogen | |
| Candida albicans | 0.5 |
| Streptococcus mutans | 2.5 |
| Staphylococcus aureus-coagulase negative | 3 |
| Commensals and Probiotics | |
| Streptococcus saliyarius (probiotic strain) | >5 |
| Streptococcus pneumonia | >10 |
| Staphylococcus epidermidis | >10 |
| Staphylococcus hominis | >10 |
| Lactobacillus bulgaricus | >10 |
| Lactobacillus casei | >10 |
| Porphyromonas gingivalis | >10 |

The conclusions that can be reached from this preliminary work are:
1. Micro-organisms that frequently cause infections (i.e. pathogens) are killed by the lowest concentrations of the combination (provided as a composition).
2. Micro-organisms that are common, harmless commensals and/or are used as probiotics were not killed by the highest concentrations tested in these trials. (100× greater than the concentration that killed pathogens).
3. Intermediate organisms, such as *Candida albicans*, which are frequently found as harmless commensals and only cause infection (i.e. become opportunistic) when the conditions change in the local environment so that growth is enhanced (e.g an increase in sugar concentration) show moderate to high MIC values.

Example 3: Comparative Selectivity Between Isolated and/or Recombined Proteins, Sub-Cationic Fractions, and Whole Cationic Fraction Additional studies were conducted which show the individual proteins in the cationic fraction (i.e. lactoperoxidase, lactoferrin, quiescin-like, jacilin-like, chitisase-like, angiogenin) have poor anti-microbial effectiveness against pathogens, and therefore will not be able to provide the selectivity offered by the combination of proteins in the preferred compositions (most preferably the full suite of proteins in the cationic fraction). The results are shown in FIGS. 5 and 6.

Informal results also showed that the middle cationic fraction (not containing lactoperoxidase or lactoferrin) has relatively poor selectivity, supporting that lactoperoxidase is an important component of the composition, but requires other protein(s) from milk in order to develop the selectivity profile observed.

Figure 5:
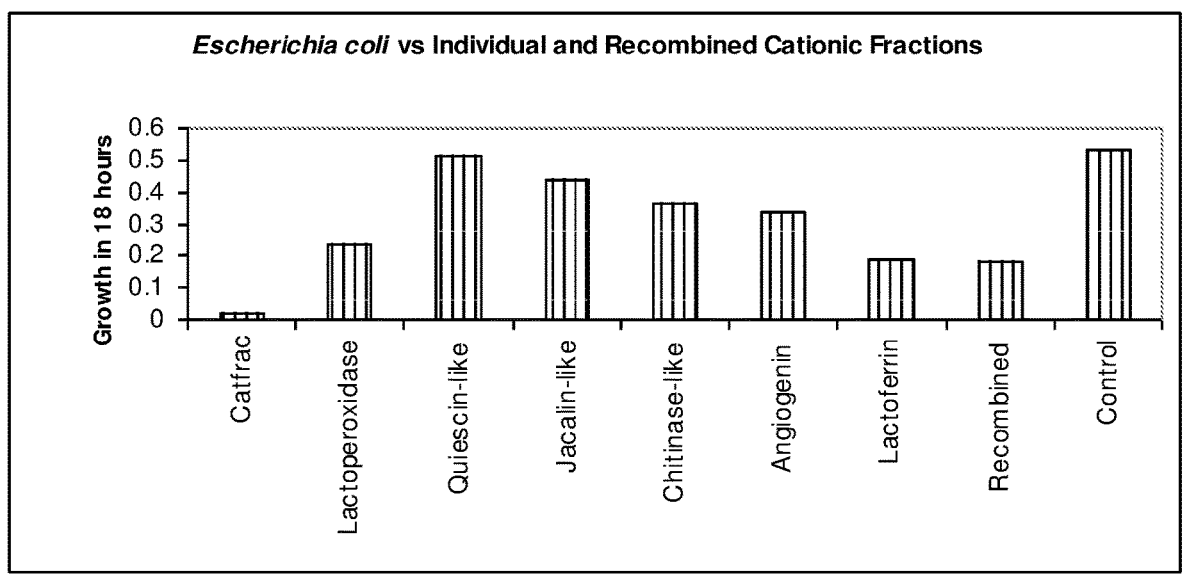
FIG. 5 shows a graph of pathogenic *Escherichia coli* growth using various sub-fractions of the cationic fraction, a recombined cationic fraction and an unfractionated (whole) cationic fraction.
Figure 6:
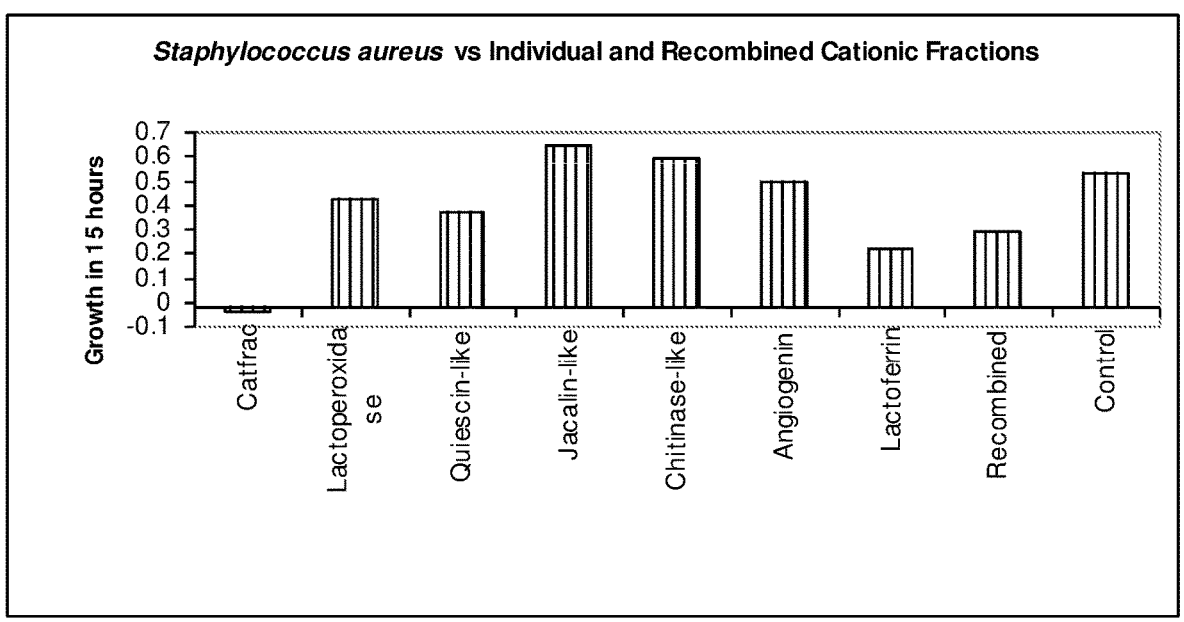
FIG. 6 shows a graph of pathogenic *Staphylococcus aureus* growth using various sub-fractions of the cationic fraction, a recombined cationic fraction and an unfractionated (whole) cationic fraction.

Also, the results shown in FIGS. 5 and 6 showed that with there is a benefit of retaining the proteins together during the extraction process, rather than isolating them and recombining to form the composition. Nonetheless, the recombined fraction provides useful inhibition of *E. coli* and *S. aureus*.

The fact that anti-microbial activity is enhanced when the cationic fraction remains intact also strongly suggests the selectivity will be better if the components are not individually separated from one another before recombining. That is, the combination is preferably provided as a composition which preferably includes the cationic fraction of milk.

Based on these results, the following schematic representation is provided to illustrate the effectiveness of the present invention towards selectivity.

|  | Low | | | | | High |
|---|---|---|---|---|---|---|
|  | | | MIC (mg/ml) | | | |
|  | <0.1 | 0.5 | 1.0 | 2.0 | 5.0 | >10.0 |
| Lactoferrin (Lf) | | | | Pathogenic-Opportunistic-Commensals (no selectivity) | | |
| Lactoperoxidase (Lp) | | | | Pathogenic-Opportunistic-Commensals (no selectivity) | | |
| Middle Cationic Fraction* | | | | Pathogenic-Opportunistic-Commensals (no selectivity) | | |
| Whole cationic fraction** | Pathogenic | Opportunistic commensals such as *C albicans* | | | Commensals | |

*e.g. angiogenin, quiescin, jacalin-like protein, and chitinase-like protein - no Lp or Lf
**as seen in Table 4.

Example 4: Effect of Additional Substrates

Figure 3:
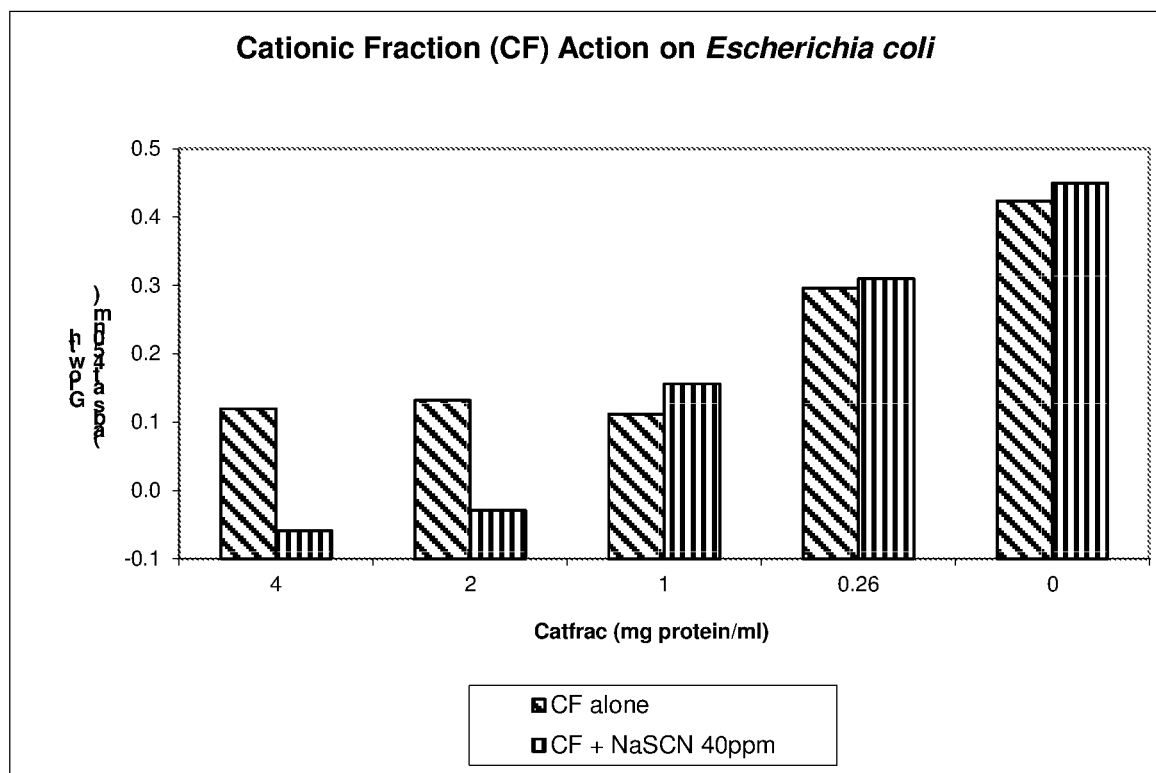
FIG. 3 shows a graph of pathogenic *Escherichia coli* inhibition using the cationic fraction alone, and with 40 ppm of sodium thiocyanate.
Figure 4:
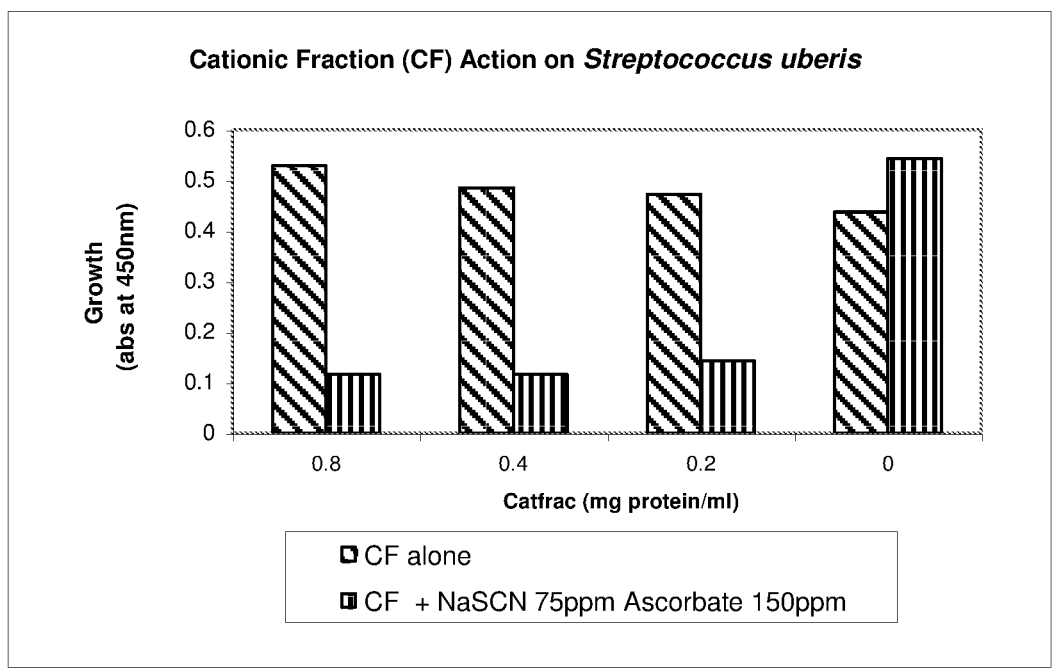
FIG. 4 shows a graph of pathogenic *Streptococcus uberis* inhibition using the cationic fraction alone, and with 75 ppm of sodium thiocyanate and 150 ppm of ascorbate.

FIGS. 3 and 4 illustrate that anti-microbial effects (and hence potentially selectivity too) are improved in the presence of substrates. If such substrates are not present at the site of infection, it may be beneficial to include suitable substrates within the combination. The extent of growth of the micro-organism is indicated by the height of the bars. The shortest bars show maximum inhibition of growth. For this figure, the left-hand bars indicate that some inhibition of growth is achieved with the cationic fraction alone at a concentration of 1 mg/ml. However, adding 40 ppm of sodium thiocyanate to the cationic fraction allowed total growth inhibition to occur at a cationic fraction concentration of 2 mg/ml. This indicates that lactoperoxidase contributes to the antimicrobial activity when its substrate (thiocyanate) is included.

FIG. 4 shows the results of a different formulation of the cationic fraction against *Streptococcus uberis*, this time using sodium thiocyanate (75 ppm) and ascorbate (150 ppm) as substrates. Against *Streptococcus uberis*, there is no inhibition in vitro using the cationic fraction alone up to 0.8 mg/ml. However, adding sodium thiocyanate and ascorbate shows an inhibitory effect occurring as low as 0.2 mg/ml of the cationic fraction. This confirms that in the absence of milk (or another natural source of substrates) the addition of thiocyanate (as substrate) and ascorbate (as a source of peroxide) may be useful for increasing inhibition (and perhaps selectivity) towards *Streptococcus uberis*.

Note that in FIG. 4, none of the additives were totally inhibitory on their own. The samples labeled '0' in the figure are buffer-only and additive-only samples.

TABLE 5

Example formulations used for comparative testing are provided below

| Combination (as a composition) | Lactoperoxidase | Lactoferrin | "Cationic fraction" | "Activated cationic fraction" |
|---|---|---|---|---|
| Lactoferrin | 0% | 92.9% | 64.3% | 61.3% |
| Lactoperoxidase | 97.7%* | 0% | 22.8% | 26.6% |
| Other protein | <2.3%* (n.m.) | 5.1% | 9.3% | 8.1% |
| Glucose | 0% | 0% | 0% | 0.845% |
| Glucose oxidase | 0% | 0% | 0% | 0.015% |
| Thiocyanate | 0.004% | 0% | 0.004% | 0.004% |
| Monolaurin | 0% | 0% | 0% | 0.25% |

*total protein value as no specific assay for lactoperoxidase is reported for this material, hence other protein level cannot be estimated.

Note:
for each sample, the remainder of material to 100% is largely inorganic (measured as ash) or residual moisture.

Note:
n.m. was not measured

Note:
there are hundreds or probably thousands of minor proteins ("other protein") within the cationic whey fraction.

It will be noted that the "activated cationic fraction" includes glucose, glucose oxidase and monolaurin which are not typically found in milk, let alone the "cationic fraction". Glucose oxidase can use glucose as a substrate to generate peroxide in situ. Other peroxide generating systems may include percarbonate or peracetate, which may be encapsulated or coated to control the release rates of the peroxides. These components may be considered to act as adjuvants.

Thiocyanate is present in the "activated cationic fraction" and is an example of a substrate. Other examples of substrates include iodide or chloride, having countercations of sodium, potassium or calcium.

The innate lactoperoxidase system protects the eyes, nose, mouth and airways from invasion by harmful microbes and requires presence of the lactoperoxidase enzyme, peroxide and thiocyanate or halide.

$H_2O_2$ is naturally present in internal biological environments as it is a by-product of various oxidative processes. For example, neutrophils produce large amounts of free peroxy radicals ($O_2^-$) of which the steady state concentration has been estimated to be in the micromolar range. (Ref. Hampton, M B, Kettle A J, Winterbourn C C. Inside the neutrophil phagosome: oxidants, myeloperoxidase, and bacterial killing. *Blood* 1998; 92:3007-17)

Peroxidases (such as lactoperoxidase) are present in biological secretions and catalyse $H_2O_2$ dependent oxidation of halides (thiocyanate, iodide, bromide, chloride) that can react with and kill microbes. (Ref. Klebanoff S J. Antimicrobial mechanisms in neutrophilic polymorphonuclear leukocytes. *Semin. Hemotol* 1975; 12:117-42)

Thiocyanate is naturally present in lymph and blood, in the mammary, salivary and thyroid glands and their secretions, in synovial, cerebral, cervical and spinal fluids and in organs such as stomach and kidney. For example, thiocyanate levels measured in human trachea-bronchial secretions from intubated adult patients were 0.46+/−0.19 mM or 26.7+/−11 ppm (range 16-38 ppm). (Ref. Wijkstrom-Frei, C., El-Chemaly, S., Ali-Rachedi, R., Gerson, C., Cobas, M. A., Forteza, R., Salathe, M. and G. E. Conner. 2003. Lactoperoxidase and human airway host defense, *Am. J. Respir. Cell Mol. Biol.*, 29:206-12).

As such, in some circumstances, such as where the combination is being applied internally, to an open wound, or to a mucosal membrane it may not be necessary, or even preferable to provide an adjuvant and/or a substrate as part of the combination since that substrate will be provided endogenously by the tissue to which the combination is applied.

In other circumstances the endogenous concentration of the adjuvant and/or substrate may be too low or non-existent to have an appreciable effect on the activity of the combination.

In those circumstances it may be preferable to include an adjuvant and/or substrate in the combination.

For in vitro testing, the assay medium will not typically contain the adjuvant and/or substrate and the improved results for the "activated cationic fraction" compared with the "cationic fraction" may be partially explained by the beneficial effect of the substrate and adjuvants contained in the activated cationic fraction. However, the "cationic fraction" may still provide useful selectivity when applied, for example, to an area of the body where the substrate and/or adjuvants (halides and peroxide generation, for example) are already present such as application internally, to an open wound, or to a mucosal membrane.

Example 5: Bacterial Selectivity

The activity and selectivity of a range of test compounds/compositions were determined against a range of pathogenic and commensal organisms.

The methodology for each of the following test compositions is described below:

Lactoperoxidase (sample 3);
Lactoferrin (sample 2);
"Cationic fraction" (sample 4); and
"Activated cationic fraction" (sample 1)

Each sample was prepared as a stock solution at 5 mg/ml. Samples 1, 3 and 4 were dissolved in HBSS which contains potassium isothiocyanate at 40 ppm (40 µg/ml). Sample 2 was dissolved in HBSS at 5 mg/ml (Table 4).

Aerobic Testing

Experiment Protocol for *C. albicans, S. aureus, S. epidermidis, S. mitis, S. mutans* and *S. salivarius*

1. For *C. albicans* Sabouraud dextrose broth powder was added to distilled water at 30 g/L and stirred. For *S. aureus* and *S. epidermidis* tryptic soy broth powder was added to distilled water at 30 g/L and stirred. For *S. mitis, S. mutans* and *S. salivarius* 5% sheep blood broth was prepared by diluting the sheep blood with double distilled water.
2. The broth solutions were then boiled for 1 minute with stirring to completely dissolve the powder.
3. The broth media were then autoclaved at 121° C. for 20 minutes.
4. A small quantity of each pure micro-organism was taken and used to inoculate 40 ml of broth medium. The inoculated broth was incubated for approximately 66 hours at 37° C.
5. The broth culture was diluted with fresh, sterile broth medium to an $OD_{650nm}$ of approximately 0.1, equivalent to approx $10^5$ CFU/ml prior to commencement of MIC testing. This is the inoculant which will be used to inoculate the test wells in each plate. The inoculant was held at 4° C. until required for plating.
6. Stock solutions of the test sample were prepared such that the concentration is 5 mg/ml in the appropriate broth.
7. The reference antibiotic was dissolved in broth to give a final concentration of 100 µg/ml.
8. 96 well microtitre plates were then set up as indicated in the plate layout diagrams below: 200 µl of the appropriate sample stock solution of test sample in the appropriate broth, antibiotic standards and vehicle control were added to the relevant wells in Column 1 on Plates 1 to 3.
9. To all other wells 100 µl of the appropriate sterile broth was added.
10. Using a multichannel pipette, 100 µl of the sample and antibiotic was sampled from the wells of column 1 on each plate and transferred to wells in column 2, mixed thoroughly by pipetting up and down 5 times. Fresh tips were added to the pipette and 100 µl of solution was transferred from the wells of column 2 to those of column 3, mixed thoroughly by pipetting up and down 5 times and then discarding the tips. This process was continued through to the wells of column 11 on each plate. This process will result in serial double-dilutions that range from 5 mg/ml to 0.005 mg/ml for samples, and 100 µg/ml to 0.098 µg/ml for the antibiotic standard. The 12th and final well in each row (Plates 1 to 3) contain wells of broth only with inoculants and broth only without inoculants (Plates 4). These wells serve as sterility control blanks and test substance free control blanks respectively.
11. Wells A1-12, 81-12, C1-12, D1-12, E1-12, F1-12, G1-12 and H1-12 on Plate 4 contain broth only and were not inoculated with seed culture. These wells served as sterility controls and blank for each row. Wells A12-F12 (Plates 1-2) and A12-C12 (Plate 3) contained the cells and serve as the negative control.
12. 100 µl of inoculant or broth were added to each well as indicated in the plate layouts below. The addition of inoculant or broth halve the extract concentration in each well giving final well concentrations ranging from 2.5 mg/ml to 0.0025 mg/ml for samples (including vehicle control) and 50 µg/ml to 0.049 µg/ml for the antibiotic standard.
13. The plates were gently tapped to ensure even mixing of the inoculant with the sample solutions.
14. The $OD_{650nm}$ of each well were read using a Versamax microtitre plate reader. This will be recorded as the zero time reading.
15. The plates were incubated for 3 hours at 37° C. at which time the $OD_{650nm}$ of each well were read and recorded as the 3 hour reading.
16. The plates were returned to the incubator for a further 13 hours and the $OD_{650nm}$ of each well was read and recorded as the 16 hour reading.
17. The microtitre plates were returned to the incubator for a further 8 hours and the $OD_{650nm}$ was read and recorded as the 24 hour reading.
18. Once the $OD_{650nm}$ of the plates was read, the wells containing the highest dilution of each sample (lowest concentration of test extract) without a detectable change in $OD_{650nm}$ in comparison to the initial reading at time zero were noted.

Anaerobic Testing
Experiment Protocol for *B. bifidum, B. breve, C. difficile, C. perfringens* and *P. acnes*

1. For each of these bacteria, Brain Heart Infusion Blood broth was used. It was prepared by adding it to distilled water at 37 g/L.
2. The broth solution was then boiled for one minute with stirring to completely dissolve the powder.
3. The broth media was then autoclaved at 121° C. for 20 minutes.
4. A small quantity of each organism was used to inoculate 40 ml of the Brain Heart Infusion broth that was de-aerated by bubbling nitrogen into it. This sealed tube is then incubated at 37'C.
5. During this incubation, the samples were prepared. Stock solutions of the samples were prepared at 5 mg/ml in the broth.
6. The reference antibiotic was dissolved in broth to give a final concentration of 100 µg/ml.
7. 96 well microtitre plates was then set up as indicated in the plate layout diagrams below: 200 µl of the appropriate sample stock solution of test sample in the appropriate broth, antibiotic standards and vehicle control) was added to the relevant wells in Column 1 on Plates 1 to 3.
8. To all other wells 100 µl of the appropriate sterile broth was added.
9. Using a multichannel pipette, 100 µl of the sample and antibiotic was sampled from the wells of column 1 on each plate and transferred to wells in column 2, mixed thoroughly by pipetting up and down 5 times. Fresh tips were added to the pipette and 100 µl of solution was transferred from the wells of column 2 to those of column 3, mixed thoroughly by pipetting up and down 5 times and then discarding the tips. This process was continued through to the wells of column 11 on each plate. This process results in serial double-dilutions that range from 5 mg/ml to 0.005 mg/ml for samples, and 100 µg/ml to 0.098 µg/ml for the antibiotic standard. The 12th and final well in each row (Plates 1 to 3) contain wells of broth only with inoculants and broth only without inoculants (Plates 4). These wells serve as sterility control blanks and test substance free control blanks respectively.
10. Wells A1-12, B1-12, C1-12, D1-12, E1-12, F1-12, G1-12 and H1-12 on Plate 4 contain broth only and are not inoculated with seed culture. These wells serve as sterility controls and blank for each row. Wells A12-F12 (Plates 1-2) and wells A12-C12 (Plate 3) contain the cells and serve as the negative control.
11. 100 µl of inoculant or broth are added to each well as indicated in the plate layouts below. The addition of inoculant or broth halve the extract concentration in each well giving final well concentrations ranging from 2.5 mg/ml to 0.0025 mg/ml for samples (including vehicle control) and 50 µg/ml to 0.049 κg/ml for the antibiotic standard.
12. The plates are gently tapped to ensure even mixing of the inoculant with the sample solutions.
13. The $OD_{650nm}$ of each well were read using a Versamax microtitre plate reader. This was recorded as the zero time reading.
14. The plates are then placed in a sealed container along with one or more anaerobic pouches. The sealed container is then incubated at 37° C.
15. After 3 hours, the plates are removed from the container and the $OD_{650nm}$ of each well are read in the platereader immediately, one plate at a time. The plates were then returned to the container along with new anaerobic pouches and plates incubated at 37° C.
16. At 16 hours after commencing the study, step 15 was repeated.
17. After 24 hours, the $OD_{650nm}$ of each well was measured.
18. Once the $OD_{650nm}$ of the plates was read, the wells containing the highest dilution of each sample (lowest concentration of test extract) without a detectable change in $OD_{650nm}$ in comparison to the initial reading at time zero was noted.

The results of the testing of the anaerobic species and the aerobic species are presented in Table 6.

TABLE 6

| | MIC values @ 3 hrs (mg/ml) | | |
|---|---|---|---|
| | Organism | | |
| Type | *Candida albicans* Commensal/ Opportunistic Pathogen | *Staphylococcus aureus* Pathogen | *Staphylococcus epidermidis* Commensal |
| Sample 1 Activated cationic fraction | 0.005 | 0.002 | 0.01 |
| Selectivity* | 2.0 | 5.0 | 1.0 |
| Sample 2 Lactoferrin | 0.625 | ≥2.5 | ≥2.5 |
| Selectivity* | ≥4.0 | — | 1.0 |
| Sample 3 Lactoperoxidase | ≥2.5 | ≥2.5 | ≥2.5 |
| Selectivity* | — | — | 1.0 |
| Sample 4 Cationic fraction | ≥2.5 | ≥2.5 | ≥2.5 |
| Selectivity* | — | — | 1.0 |

| | MIC values @ 48 hrs (mg/ml) | | |
|---|---|---|---|
| | Organism | | |
| Type | *Streptococcus mitis* Commensal | *Streptococcus mutans* Pathogen | *Streptococcus salivarius* Commensal |
| Sample 1 Activated cationic fraction | 0.625 | 0.002 | 0.156 |
| Selectivity* | 1.0 | 78.0-300** | 1.0 |
| Sample 2 Lactoferrin | 1.25 | ≥2.5 | 2.5 |
| Selectivity* | ≥2.0 | — | 1.0 |
| Sample 3 Lactoperoxidase | ≥2.5 | ≥2.5 | ≥2.5 |
| Selectivity* | — | — | 1.0 |
| Sample 4 Cationic fraction | ≥2.5 | ≥2.5 | ≥2.5 |
| Selectivity* | — | — | 1.0 |

*1.0 = no selectivity
**relative to *S. salivarius* and *S. mitis*

Aspects of the present invention have been described by way of example only and it should be appreciated that modifications and additions may be made thereto without departing from the scope thereof.

The invention claimed is:

1. A method of modulating a microbiome by selectively inhibiting growth or killing pathogenic micro-organism *Streptococcus pyogenes* without a comparative inhibition of at least one commensal micro-organism, the method comprising the step of administering to a human tissue including a microbiome a combination including:
   lactoperoxidase present at a minimum amount of at least 5% w/w;
   angiogenin;
   lactoferrin;

lysozyme-like protein;
quiescin; and
jacalin-like protein,
   wherein the lactoperoxidase, angiogenin, lactoferrin, lysozyme-like protein, quiescin, and jacalin-like protein all have an isoelectric point of or above 6.8 and are extracted from milk from a non-human species.

2. The method according to claim 1 wherein the combination is a composition.

3. The method according to claim 2 wherein the lactoperoxidase and angiogenin are in intimate admixture in the milk and remain in intimate admixture in the formation of the composition.

4. The method according to claim 1 wherein the combination is applied externally.

5. The method according to claim 1 wherein the combination is applied internally.

6. The method according to claim 1 wherein the combination further includes proteins isolated from milk which have an isoelectric point of or above 6.8.

7. The method according to claim 1 wherein the commensal micro-organism is selected from: *Staphylococcus epidermidis, Streptococcus pneumonia, Staphylococcus hominis, Lactobacillus bulgaricus, Lactobacillus casei, Porphyromonas gingivalis, Streptococcus mitis* and *Streptococcus salivarius*.

8. The method according to claim 1 wherein the combination further includes one or more components selected from substrates.

9. The method according to claim 8 wherein the one or more component substrates includes a peroxidase substrate.

10. The method according to claim 1 wherein the combination further includes thiocyanate.

11. The method according to claim 1 wherein the combination further includes one or more components selected from: cathelicidin 1; N-acetyl glucosaminidase; serum amyloid A; β Defensin; Peptidoglycan recognition protein; Xanthine dehydrogenase; Immunoglobulin(s) IgA, IgD, IgG, IgM, IgA, and/or IgE; and/or Growth factors EGF, IGF 1, TGF B1 and TGF B2.

12. The method according to claim 1 wherein the combination selectively inhibits growth of *Streptococcus pyogenes* by a multiple of at least 1.1 compared with the degree of inhibition of at least one commensal micro-organism.

13. The method according to claim 1 wherein the human tissue is at least part of skin, conjunctiva, nose, pharynx, lower gastrointestinal tract, anterior urethra, or vagina.

* * * * *